United States Patent [19]
Knutson et al.

[11] Patent Number: 5,801,164
[45] Date of Patent: Sep. 1, 1998

[54] METHODS OF TREATING OSTEOPOROSIS PROPHYLACTICALLY OR THERAPEUTICALLY

[75] Inventors: Joyce C. Knutson, Madison; Charles W. Bishop, Verona, both of Wis.; Robert M. Moriarty, Oak Park, Ill.

[73] Assignee: Bone Care International, Inc., Madison, Wis.

[21] Appl. No.: 480,310

[22] Filed: Jun. 7, 1995

Related U.S. Application Data

[62] Division of Ser. No. 265,438, Jun. 24, 1994, which is a continuation of Ser. No. 886,554, May 20, 1992, abandoned, which is a continuation-in-part of Ser. No. 800,045, filed as PCT/US91/06865, Sep. 20, 1991, abandoned, which is a continuation of Ser. No. 586,854, Sep. 21, 1990, abandoned.

[51] Int. Cl.$^6$ .................................................. A61K 31/59
[52] U.S. Cl. ............................................................. 514/167
[58] Field of Search ............................................... 514/167

[56] References Cited

U.S. PATENT DOCUMENTS

| | | |
|---|---|---|
| 2,383,446 | 6/1945 | Calcott et al. . |
| 3,697,559 | 10/1972 | DeLuca et al. . |
| 3,741,996 | 6/1973 | DeLuca et al. . |
| 4,195,027 | 3/1980 | DeLuca et al. . |
| 4,202,829 | 5/1980 | DeLuca et al. . |
| 4,241,051 | 12/1980 | Christie et al. ............ 424/177 |
| 4,260,549 | 4/1981 | DeLuca et al. . |
| 4,362,710 | 12/1982 | Watanabe . |
| 4,555,364 | 11/1985 | DeLuca et al. . |
| 4,661,294 | 4/1987 | Holick et al. . |
| 4,689,180 | 8/1987 | DeLuca et al. . |
| 4,866,048 | 9/1989 | Calverley et al. . |
| 5,157,135 | 10/1992 | Tsuji et al. . |

FOREIGN PATENT DOCUMENTS

| | | |
|---|---|---|
| A-0 390 097 | 10/1990 | European Pat. Off. . |
| BE-A-877 356 | 10/1979 | France . |
| WO 79/00513 | 1/1979 | WIPO . |
| PCT/DK86/00081 | 2/1987 | WIPO . |
| PCT/US90/00954 | 9/1990 | WIPO . |

OTHER PUBLICATIONS

Martin, D. L. and DeLuca, H. F. *Arch. Biochem, Biophys.*, 134:139–148 (1969).

Sorenson, O.H. et al, 7 *Clin. Endocr.* (1977) Supp. 169S–175S.

E. Braunwald et al., *Harrison's Principles of Internal Medicine:* Part Eleven, "Disorders of Bone and Mineral Metabolism," Chapter 335, McGraw–Hill, New York, 1987, pp. 1860–1865.

Grab, W., *Z. Physiol. Chem.*, 243:63–89 (1936).

McDonald, F. G., *J. Biol. Chem.*, 114:IVX (1936).

Windaus, A. and Trautmann, G., *Z. Physiol. Chem.*, 247:185–188 (1937).

DeLuca et al., *Arch. Biochem, Biophys.*, 124:122–128 (1968).

*Merck Index*, S. Budavari (ed.), 11th ed., Merck & Co., Rahway, N.J. (1989) pp. 1579, #9930.

Barton et al., *JCS Perkin I*, 1976, 821–826.

Paaren et al., *J. Org. Chem.*, 1980, 45:3253.

Wientroub, S. et al., "The Dichotomy in the Effects of 1,25 dihydroxy vitamin $D_3$ and 24,25 dihydroxy vitamin $D_3$ on Bone Gamma–Carboxyglutamic Acid–Containing Protein in Serum and Bone in vitamin D–Deficient Rats," *Calcif, Tissue Int.* (1987) 40:166–172.

Sjoden, G. et al., *Proc. Soc. Experimental Biol. Med.*, 178:432–436 (1985).

Strugnell et al., *Biochem. Pharm.* vol. 40:333–341 (1990).

Martin and DeLuca, *Am. J. Physiol.* 216:1352–1359.

Kocienski, P. J., Lythgoe, B. and Ruston, S., *J.C.S. Perkins I*, 1290–1293 (1979).

Tsuji, M. et al., *Bull. Chem. Soc. Jpn.*, vol. 63, No. 8, 2233–2238 (1990).

Crump, D. R., Williams, D. H. and Pelc, B., *J.C.S. Perkins Trans. I*, 2731–2733 (1973).

Chemical Abstracts, vol. 113, No. 1, 2 Jul. 1990, Columbus, Ohio, US; abstract No. 6683y, Y. Tachibana, 'Preparation of 1beta–hydroxyvitamin $D_2$ and $D_3$,' p. 6688; col. 2; *abstract* & JP–A–02 011 563 (Nisshin Flour Milling Co.).

Chemistry Letters, No. 8, Aug. 1985, Tokyo, JP, pp. 1131–1132, H. Nemeto et al., 'A stereoselective synthesis of 1 alpha–hydroxy–vitamin $D_3$', *the whole document*.

*Primary Examiner*—José G. Dees
*Assistant Examiner*—Barbara Badio
*Attorney, Agent, or Firm*—Teresa J. Welch; Stroud, Stroud, Willink, Thompson & Howard

[57] ABSTRACT

Methods of treating osteoporosis prophylactically or therapeutically are disclosed. The method of treating osteoporosis includes administering to a patient suffering therefrom an effective amount to treat the osteoporosis of novel 1α-hydroxyvitamin $D_4$ and novel analogues 1,25-dihydroxyvitamin $D_4$ and 1,24-dihydroxyvitamin $D_4$, the aforementioned compounds having lower toxicity as measured by an $LD_{50}$ test in rats when compared to a corresponding vitamin $D_3$ compound. The method of administering the compound is substantially without occurrence of hypercalcemia.

11 Claims, 2 Drawing Sheets

5,801,164

METHODS OF TREATING OSTEOPOROSIS PROPHYLACTICALLY OR THERAPEUTICALLY

This is a division of application Ser. No. 08/265,438 filed Jun. 24, 1994, which is a continuation of application Ser. No. 07/886,554, filed May 20, 1992, now abandoned which is a continuation-in-part of application Ser. No. 07/800,045, filed Nov. 29, 1991, now abandoned, and a Section 371 of PCT/US91/06865, which is a continuation of application Ser. No. 07/586,854, filed Sep. 21, 1990, now abandoned.

TECHNICAL FIELD

This invention relates to biologically active vitamin $D_4$ compounds. More specifically, this invention relates to novel $1\alpha$-hydroxy vitamin $D_4$ and novel intermediates used in its synthesis, novel 1,25 dihydroxy vitamin $D_4$, and novel 1,24 dihydroxy vitamin $D_4$.

This invention also relates to a pharmaceutical composition which includes a pharmaceutically effective amount of the novel $1\alpha$-hydroxy vitamin $D_4$ compounds, and to a method of controlling abnormal calcium metabolism by administering a pharmaceutically effective amount of the novel compounds.

BACKGROUND

Vitamin D is known to be important in the regulation of calcium metabolism in animals and man. See, *Harrison's Principals of Internal Medicine*: Part Eleven, "Disorders of Bone and Mineral Metabolism, Chapter 335," E. Braunwald, et al., (eds.), McGraw-Hill, New York, 1987, pp. 1860–1865. The two most commonly known, useful forms of vitamin D are vitamin $D_3$ and vitamin $D_2$. Vitamin $D_3$ is synthesized endogenously in the skin of animals and man, whereas vitamin $D_2$ is the form of vitamin D supplied by plants. Vitamin $D_2$ differs from vitamin $D_3$ in that it contains a double bond between C22 and C23 and further contains a C24-methyl group. In man and rats, vitamin $D_3$ and vitamin $D_2$ have equivalent biopotency.

Vitamin $D_4$, also known as irradiated 22,23-dihydroergosterol or 22,23-dihydro vitamin $D_2$ or 22,23-dihydroergocalciferol, differs from vitamin $D_3$ in that it contains a C24 methyl group. Vitamin $D_4$ was first described in 1936. See, Grab, W., *Z.Physiol. Chem.*, 243:63 (1936); McDonald, F. G., *J. Biol. Chem.*, 114:IVX (1936). See also, Windaus, A. and Trautmann, G., *Z. Physiol. Chem.*, 247:185–188 (1937). These references report some disagreement as to the level of biological activity of the vitamin suggesting that in the rat, vitamin $D_4$ is one-third or three-fourths as active as vitamin $D_3$ and in the chick, either one-tenth or one-fifth as active as vitamin $D_3$.

A more definitive study of the biological activity of vitamin $D_4$ was made by DeLuca, et al., in 1968. DeLuca, et al., *Arch. Biochem. Biophys.*, 124:122–128 (1968). There, the authors confirmed that vitamin $D_4$ was less active than vitamin $D_3$. DeLuca, et al., report that, in their hands, vitamin $D_4$ is two-thirds as active as vitamin $D_3$ or vitamin $D_2$ in the rat, and one-fifth as active as vitamin $D_3$ in the chick.

DeLuca, et al., make reference to the fact that "[t]he synthesis of vitamin $D_4$ has apparently been little used since it was first described by Windhaus and Trautmann," and comment, "[t]his is perhaps due to the fact that vitamin $D_4$ is only of academic interest."

To applicants' knowledge, vitamin $D_4$ has remained "only of academic interest" as applicants are unaware of any further study of vitamin $D_4$ since that reported by DeLuca, et. al. In fact, *The Merck Index* states with respect to vitamin $D_4$, "Its biological activity seems doubtful." *Merck Index*, S. Budavari (ed.), 11th ed., Merck & Co., Rahway, N.J., (1989) pp. 1579, #9930.

Since DeLuca, et. al., discovered the active form of vitamin $D_3$, 1,25-dihydroxy vitamin $D_3$, (U.S. Pat. No. 3,697,559) and its synthetic precursor, $1\alpha$-hydroxy vitamin $D_3$, (U.S. Pat. No. 3,741,996), most interest has centered on developing therapeutic uses of these active vitamin $D_3$ metabolites. Unfortunately, while the vitamin $D_3$ metabolites held great promise as therapeutic agents, this promise has never been fully realized because of the extreme toxicity of these agents. For example, toxicity limits the efficacy of vitamin $D_3$, its active forms and analogs, to prevent bone loss or restore lost bone. Many studies indicate that at dosages required for these agents to be effective in bone loss prevention or restoration, hypercalcemia and hypercalciuria are problems. It has been reported that $1\alpha$-hydroxy vitamin $D_3$ at a daily dose of 2 μg/day (which has been shown in some studies to be effective in preventing loss of bone) causes toxicity in approximately 67% of patients. What is needed is a biopotent vitamin D metabolite of low toxicity, such that the drug is practical as a therapeutic agent.

SUMMARY OF THE INVENTION

The novel compounds of the invention, $1\alpha$-hydroxy vitamin $D_4$, 1,25-dihydroxy vitamin $D_4$ and 1,24-dihydroxy vitamin $D_4$, are bioactive forms of vitamin $D_4$. The present inventors have discovered that these active forms of vitamin $D_4$ display much greater biopotency than would be predicted on the basis of the previously reported bioassays of vitamin $D_4$. The present inventors have also discovered, that the bioactive novel compounds are less toxic than would be predicted on the basis of their biopotency. This combination of high activity with low toxicity makes the compounds of the invention useful as therapeutic agents in the treatment of disorders of calcium metabolism. The novel compounds of the invention are advantageously used as the active compounds of pharmaceutical compositions for diseases induced by abnormal metabolism of calcium.

In order to study the novel compounds of the invention, it was necessary to develop processes for their production. One alpha-hydroxy vitamin $D_4$ was made synthetically and in the course of that synthesis, novel intermediates were also produced. 1,25-dihydroxy vitamin $D_4$ and 1,24-dihydroxy vitamin $D_4$ are isolated as biological products of the metabolism of $1\alpha$-hydroxy vitamin $D_4$.

Other advantages and a fuller appreciation of the specific adaptations, compositional variations, and physical and chemical attributes of the present invention will be gained upon an examination of the following detailed description of the invention, taken in conjunction with the accompanying drawings.

BRIEF DESCRIPTION OF THE DRAWINGS

The present invention will hereinafter be described in conjunction with the appended drawings, wherein like designations refer to like elements throughout and in which.

DETAILED DESCRIPTION

The present invention provides synthetic $1\alpha$-hydroxy vitamin $D_4$ ($1\alpha$—OH—$D_4$) compounds as well as tosylated and cyclic derivatives of vitamin $D_4$.

As used herein, the terms "biological activity" or "biologically active" are meant to refer to biochemical properties of compounds such as affecting metabolism, e.g., affecting serum calcium concentration, or binding to an appropriate receptor protein, e.g., binding to vitamin D recepter protein.

In one of its aspects, the invention encompasses biologically active compounds of the general formula (I):

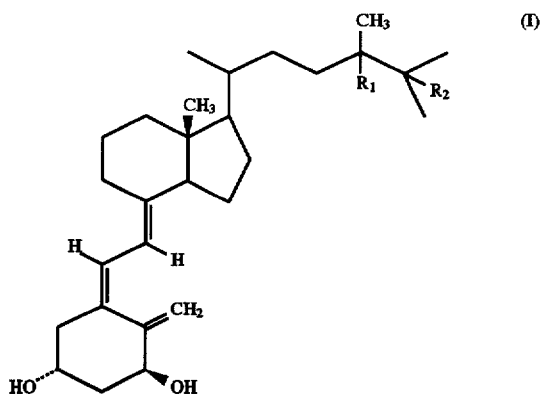

wherein $R_1$ is either H or OH, and $R_2$ is either H or OH, and salts, hydrates and solvates thereof. Preferred compounds among those of formula (I) are those in which $R_1$ and $R_2$ are both H; $R_1$=OH and $R_2$=H; and $R_1$ H and $R_2$=OH.

Figure 1:
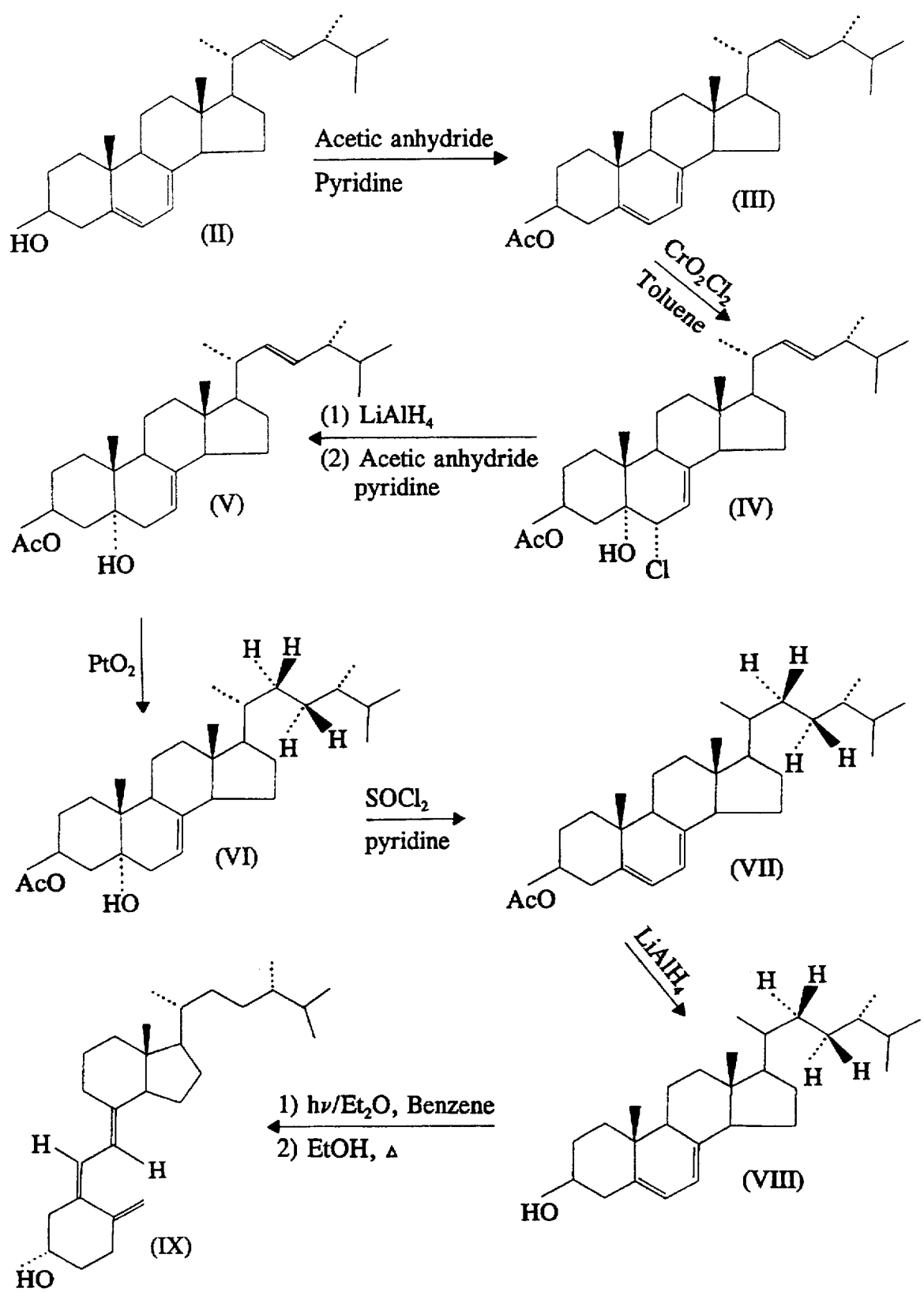
FIG. 1 illustrates preparative steps for the synthesis of vitamin $D_4$.
Figure 2:
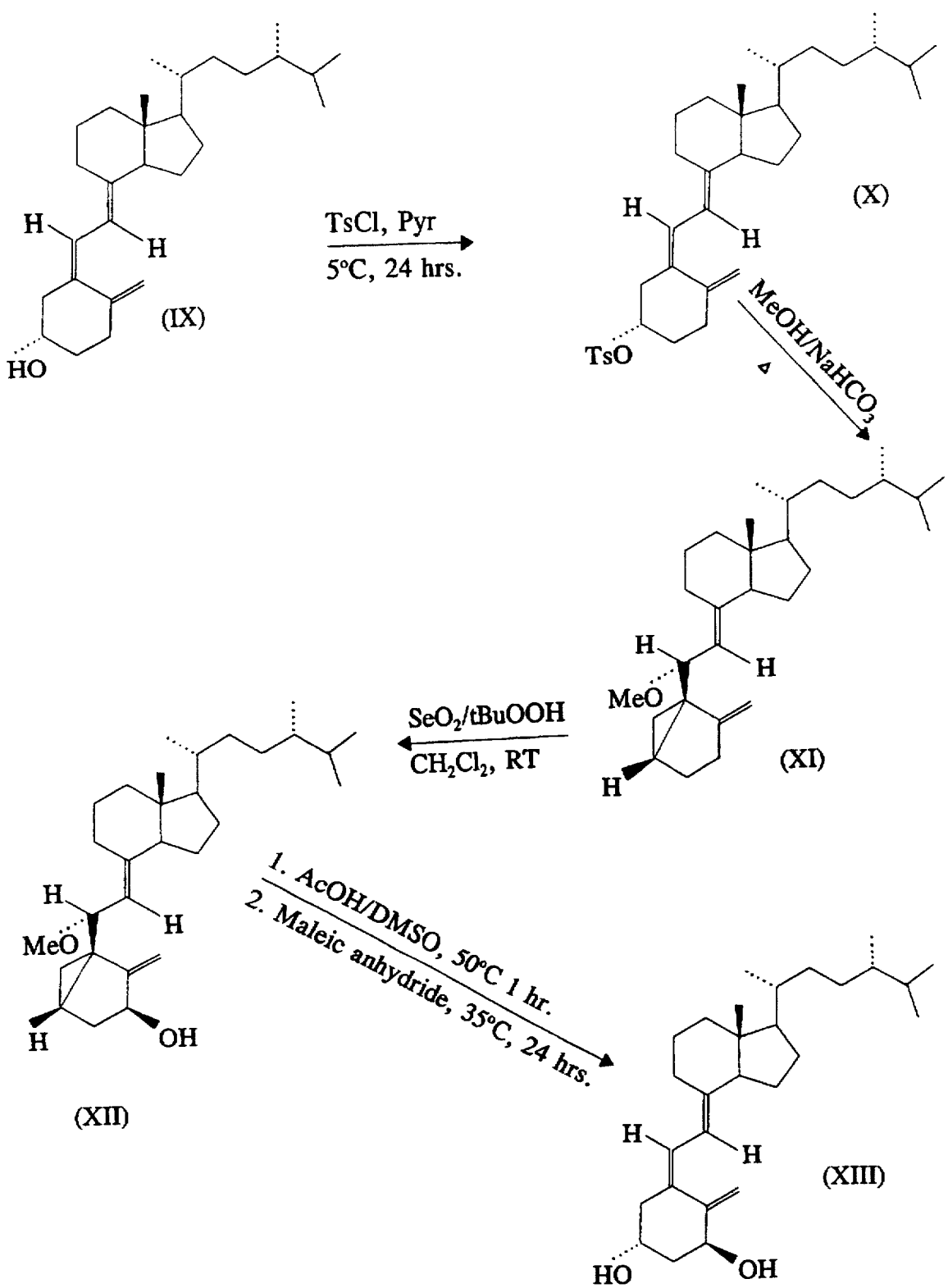
FIG. 2 illustrates preparative steps for the synthesis of $1\alpha$-hydroxy vitamin $D_4$ starting with vitamin $D_4$.

In another aspect, the invention involves the preparation of compounds of formula (I). Synthesis of 1α-hydroxy vitamin $D_4$, i.e., compounds of formula (I) wherein $R_1$ and $R_2$ are H, is accomplished according to the schema presented in FIGS. 1 and 2. As seen in FIG. 1, the synthesis uses ergosterol as the starting material. Ergosterol undergoes side chain saturation in a six-step process to yield 22,23-dihydroergosterol (VIII) using a procedure similar to that of Barton, et al., *JCS Perkin I*, 1976, 821–826. The 22,23-dihydroergosterol is then irradiated as described in windaus, et al., *Z. Physiol. Chem.*, 1937, 147:185, to yield vitamin $D_4$ [22,23-dihydroergocalciferol] (IX). As seen in FIG. 2, vitamin $D_4$ is then hydroxylated in a four-step process to yield 1α-hydroxy vitamin $D_4$ using a procedure similar to that described by Paaren, et al., *J. Org. Chem.*, 1980, 45:3253.

Specifically, ergosterol is acetylated to form the 3β-acetate. This ergosterol acetate is subjected to hydroxyhalogenation at the 5,6 double bond to form the 6α-chloro-5α-hydroxy derivative. This chlorohydrin is reduced and reacetylated to the 5α-hydroxy (i.e., 5α-ol) derivative. The 5α-ol is subjected to hydrogenation to saturate the side chain. The-resulting 3β-acetoxyergost-7en-5α-ol is reduced to 22,23 dehydroergosterol acetate which is in turn reduced to yield 22,23 dehydroergosterol. The 22,23 dehydroergosterol is then irradiated to form vitamin $D_4$. Vitamin $D_4$ is then tosylated to yield 3β-tosyl vitamin $D_4$. The tosylate is displaced by solvolysis to yield the 6-methoxy-3,5-cyclovitamin $D_4$. The cyclovitamin $D_4$ is subjected to allyllic oxidation to form the 1α-hydroxy cyclovitamin derivative. The 1α-hydroxy cyclovitamin derivative is sequentially solvolyzed and subjected to a Diels-Alder-type reaction which removes the 5-methoxy group and separates the 1α-hydroxy vitamin $D_4$ (5,6-cis) from the 5,6 trans-1α-hydroxy vitamin $D_4$.

The 1,24 dihydroxy vitamin $D_4$ and 1,25 dihydroxy vitamin $D_4$ metabolites of 1α-hydroxy vitamin $D_4$, are synthesized by incubating the 1α-hydroxy derivatives with human liver cells, culturing the cells, and recovering the 1,24 dihydroxy or 1,25 dihydroxy vitamin $D_4$. Using vitamin D receptor protein binding tests, these metabolites are determined to be biologically active.

The compounds of formula (I) have been found to possess valuable pharmacological activity, namely, as controlling agents for calcium metabolism, especially serum calcium concentrations. Specifically, the compounds of formula (I) increase serum calcium concentrations in rats with vitamin D deficiency. It has also been found that the compounds of formula (I) have low toxicity, which enhances their pharmaceutical properties. Compounds of formula (I) have a toxicity, as measured by the $LD_{50}$ test, which is similar to that of corresponding vitamin $D_2$ compounds and lower than that of corresponding vitamin $D_3$ compounds. Thus, the compounds of the invention are applicable to various clinical and veterinary fields, and are particularly useful for the treatment of abnormal metabolism of calcium and phosphorus.

In a further aspect, the invention entails a method of controlling calcium metabolism, such as for treating abnormal calcium metabolism caused, e.g., by liver failure, renal failure, gastrointestinal failure, etc. The compounds of formula (I) can be used to treat prophylactically or therapeutically vitamin D deficiency diseases and related diseases, for example, renal osteodystrophy, steatorrhea, anticonvulsant osteomalacia, hypophosphatemic vitamin D-resistant rickets, osteoporosis, including postmenopausal osteoporosis, senile osteoporosis, steriod-induced osteoporosis, and other disease states characteristic of loss of bone mass, pseudodeficiency (vitamin D-dependent) rickets, nutritional and malabsorptive rickets, osteomalacia and osteopenias secondary to hypoparathyroidism, post-surgical hypoparathyroidism, idiopathic hypoparathyroidism pseudohypoparathyroidism and alcoholism. The compounds of formula (I), preferably those wherein $R_2$ is OH, such as 1α, 24 dihydroxy vitamin $D_4$, are of value for the treatment of hyperproliferative skin disorders such as psoriasis.

The compounds of formula (I) are useful as active compounds in pharmaceutical compositions having reduced side effects and low toxicity as compared with the known analogs of active forms of vitamin $D_3$, when applied, for example, to diseases induced by abnormal metabolism of calcium. These pharamaceutical compositions constitute another aspect of the invention.

The pharmacologically active compounds of this invention can be processed in accordance with conventional methods of pharmacy to produce medicinal agents for administration to patients, e.g., mammals including humans. For example, the compounds of formula (I) can be employed in admixtures with conventional excipients, e.g., pharmaceutically acceptable carrier substances suitable for enteral (e.g., oral), parenteral, or topical application which do not deleteriously react with the active compounds.

Suitable pharmaceutically acceptable carriers include but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, vitamin $D_3$ or D2 and their 1α-hydroxylated metabolites, conjugated estrogens or their equivalents, anti-estrogens, calcitonin, biphosphonates, calcium supplements, cobalomin, pertussis toxin and boron.

For parenteral application, particularly suitable are injectable, sterile solutions, preferably oily or aqueous solution, as well as suspensions, emulsions, or implants, including suppositories. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired.

Sustained or directed release compositions can also be formulated, e.g., liposomes or those in which the active compound is protected with differentially degradable coatings, e.g., by microencapsulation, multiple coatings, etc.

For topical application, suitable nonsprayable viscous, semi-solid or solid forms can be employed which include a carrier compatible with topical application and having a dynamic viscosity preferably greater than water. Suitable formulations include, but are not limited to, solutions, suspensions, emulsions, creams, ointments, powders, liniments, salves, aerosols, transdermal patches, etc., which are, if desired, sterilized or mixed with auxiliary agents, e.g., preservatives, stabilizers, demulsifiers, wetting agents, etc.

For rectal administration, compounds are formed into a pharmaceutical composition containing a suppository base such as cacao oil or other triglycerides. To prolong storage life, the composition advantageously includes an antioxidant such ascorbic acid, butylated hydroxyanisole or hydroquinone.

Oral administration of the pharmaceutical compositions of the present invention is preferred. Generally, the compounds of this invention are dispensed by unit dosage form comprising about 0.5 µg to about 25 µg in a pharmaceutically acceptable carrier per unit dosage. The dosage of the compounds according to this invention generally is about 0.01 to about 0.5 µg/kg/day, preferably about 0.04 to about 0.3 µg/kg/day.

It will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on the age, body weight, general state of health, sex, on the diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

In a still further aspect, the compounds of the present invention can also be advantageously used in veterinary compositions, for example, feed compositions for domestic animals to treat or prevent hypocalcemia. Generally, the compounds of the present invention are dispensed in animal feed such that normal consumption of such feed provides the animal about 0.01 to about 0.5 µg/kg/day.

The following examples are to be construed as merely illustrative, and not limitative of the remainder of the disclosure in any way whatsoever. In the following examples, all temperatures are set forth in degrees Celsius; unless otherwise indicated, all parts and percentages are by weight. Proton nuclear magnetic ($^1$H NMR) spectra were recorded with an IBM Sy-200(200 mHz) and a Bruker Am—400(400 mHz) with aspect 3000 Computer in $CDCl_3$ solutions with $CHCl_3$ as an internal standard. Infrared spectra were recorded with a Fourier transform (FTIR) using samples as potassium bromide (KBr) pellets or as liquids. Mass spectra were recorded with a Finnigan MAT-90 mass spectrometer at 20 eV/CI. Melting points are determined on a Hoover-Thomas (capillary) Uni-Melt and a Fisher-Johns melting point apparatus (cover-slip type).

EXAMPLE 1

Synthesis of 1α-hydroxy vitamin $D_4$

Ergosterol (II) was converted to ergosterol acetate (III) by dissolving 100 g (0.25 mol) ergosterol in 600 ml of anhydrous pyridine and 68 ml (0.7 mol) acetic anhydride. The solution was stirred overnight at room temperature after which time the solution was cooled by adding 1.2 L ice, causing a precipitate to form. The precipitate was washed five times with 400 ml portions of water, then once with 400 ml of $CH_3CN$. The resulting product was air dried to yield 79 g (71%) of ergosterol acetate as a white crystalline solid and had the following characteristics: melting point (m.p.): 169°–171° C.; $^1$H NMR: (400 MHZ, $CDCl_3$), δppm 2.05 (3H, s, 3β-$CH_3CO$), 4.65–4.75 (1H, m, 3α-H) 5.15–5.25 (2H, m, 22-H and 23-H), 5.4 (1H, d, 6-H), 5.6 (1H, d, 7-H); FTIR [KBr]: 1734 $cm^{-1}$ (C=O stretching) 968 $cm^{-1}$ (C—H bending).

Ergosterol acetate (III) (26 gm, 0.062M) was dissolved in 2.5 L of freshly distilled deoxygenated toluene. To this solution 9 ml (0.111 mol) chromyl chloride dissolved in 240 ml dry $CH_2Cl_2$ was added under nitrogen at −78° C. over a thirty minute period. The reaction system was stirred at −78° C. for an additional fifteen minutes, and then 62 ml of a saturated solution of sodium borohydride in ethanol was added in one portion. After stirring at −78° C. for an additional fifteen minutes, the reaction solution was poured into a two phase system of 3N hydrochloric acid (3 L) and benzene (3 L). The organic layer was separated, then washed with water (2 L), twice with a brine solution (2×1 L) and then dried with anhydrous $MgSO_4$. The dried solution was filtered and concentrated in vacuo. The crude crystalline product was then treated with $CH_3CN$ (280 ml) and filtration of the thus formed slurry yielded 12.5 g (41%) of white crystalline 3β-Acetoxy-6α-chloroergosta-7,22-dien-5α-ol (IV) and had the following characteristics: m.p.: 190°–192° C.; $^1$H NMR: (400 MHz, $CDCl_3$), δppm 2.05 (3H, s, 3β-OAc), 4.65 (1H, d, 6β-H), 5.1 (1H, s, 7-H), 5.1–5.3 (2H, m, 22-H and 23-H); FTIR [KBr]: 1732 $cm^{-1}$ (C=O stretching), 968 $cm^{-1}$ (C—H bending), 3437 $cm^{-1}$ (O—H stretching).

The 3β-Acetoxy 6α-chloroergosta-7,22-dien-5α-ol (IV) (21.4 g, 0.044 mol) in dry THF (900 ml) was added slowly to a stirred suspension of lithium aluminium hydride (2.66 g, 0.07 mol) in dry THF (750 ml) at room temperature under nitrogen. The mixture was refluxed for three hours and cooled to 0° C. Excess hydride was decomposed with saturated $Na_2SO_4$ solution. Filtration through anhydrous $Na_2SO_4$ and evaporation of the filtrate gave a solid, which was treated directly with acetic anhydride (110 ml) and dry pyridine (220 ml) at 0° C. Removal of solvent under reduced pressure yielded the acetate (12.75 g, 61%), 3β-Acetoxyergosta-7,22-dien-5α-ol (V) and had the following characteristics: m.p.: 229°–232° C.; FTIR [KBr] 1736 $cm^{-1}$ (C=O stretching), 3460 $cm^{-1}$ (O—H stretching), 972 $cm^{-1}$ (C—H bending).

3β-Acetoxyergosta-7,22-dien-5α-ol (V) (2.5 g, 0.0055 mol) was shaken for sixteen hours with freshly prepared $PtO_2$ (0.5 g) in ethyl acetate (820 ml) under $H_2$ gas (15 psi).

The catalyst was removed by filtration and evaporation of the filtrate gave the crude acetate which was dissolved in $CH_2Cl_2$ and chromatographed on silica gel. Elution with $CH_2Cl_2$ gave substantially pure 3β-Acetoxyergost-7-en-5α-ol (VI) (2.15 g, 85%) as a white crystalline material and had the following characteristics: m.p.: 228°–232° C.; $^1$H NMR: (400 MHz, $CDCl_3$), δppm 2.05 (3H, s, 3β-OAc), 5.05–5.20 (2H, m, 3α-H and 7-H); FTIR [KBr]: 1736 $cm^{-1}$ (C=O stretching), 3462 $cm^{-1}$ (O—H stretching).

Redistilled thionyl chloride (9.7 ml) in dry pyridine (170 ml) was added to compound 3β-Acetoxyergost-7-en-5α-ol (VI) (12.0 g, 0.0262 mol) in dry pyridine (800 ml) at 0° C. under nitrogen. After 2.5 hours, the solution was diluted with ice cold $H_2O$ (1.5 L) and extracted with two portions of ether (2.5 L+1.5 L). The combined ether extracts were washed with a $NaHCO_3$ solution (1.0 L×2), then 1N HCl (1.5 L×2) and then water (1 L). The ether solution was dried with $MgSO_4$, and after filtration, evaporated under reduced pressure to yield a crude product which was converted to a slurry with $CH_3CN$ (100 ml). The product was collected by filtration and recrystallized from $CH_3CN$ to yield 4.5 g. (39%) of a white crystalline 22,23-dihydroergosteryl acetate (VII) and had the following characteristics: m.p.: 144°–147° C.; $^1$H NMR: (400 MHz, $CDCl_3$), δppm 2.05 (3H, s, 3β-OAc), 4.65–4.75 (1H, m, 3α-H), 5.4 (1H, d, 6-H), 5.6 (1H, d, 7-H); FTIR [KBr]: 1734 $cm^{-1}$ (C=O stretching).

22,23-dihydroergosteryl acetate (VII) (4.8 g, 0.011 mol) was added at once to a stirred suspension of lithium aluminium hydride (2.5 g, 0.066 mol) in dry ether (1.1 L) at room temperature. The mixture was stirred for two hours at room temperature. 5N NaOH was added to destroy excess lithium aluminium hydride and $H_2O$ (500 ml) was then added. The aqueous solution was then extracted with four 250 ml portions of ether. The combined ether extracts and combined organic layer were washed with brine solution (1 L), then dried with $Na_2SO_4$. Evaporation of ether under reduced pressure gave the compound, 22,23-dihydroergosterol, (VIII) (4.1 g, 94%) as a white crystalline material and had the following characteristics: m.p.: 147°–150° C.; $^1$H NMR: (400 MHz, $CDCl_3$), δppm 3.6–3.7 (1H, m, 3α-H), 5.4 (1H, d, 6H), 5.6 (1H, d, 7-H); FTIR [KBr]: 3400 $cm^{-1}$ (O—H stretching).

22,23-dihydroergosterol (VIII) (2.0 g, 5.0 mmol) was dissolved in a solution of diethyl ether and benzene (4:1, 600 ml) and irradiated (Hannovia immersion lamp, 450 watts) with stirring under argon in a water-cooled quartz vessel for three hours. The solution was concentrated in vacuo to yield a gummy solid, which was redissolved in 100 ml of ethanol and heated at reflux under argon for eight hours. Then, the solution was concentrated in vacuo and the residue was adsorbed on a silica gel column and eluted with 30% ethyl acetate in hexane to afford vitamin $D_4$ (22,23-dihydroergocalciferol) (IX) with a yield of 1.2 g. (60%) and with the following characteristics: $^1$H NMR: (400 MHz, $CDCl_3$), δppm 0.55 (3H, s, 18-$H_3$) 0.78 (6H, dd, 26-$H_3$ and 27-$H_3$) 0.87 (3H, d, 21-$H_3$) 0.93 (3H, d, 28-$H_3$) 3.94 (1H, m, 3-H) 4.82 (1H, m (sharp), 19-H), 5.04 (1H, m (sharp), 19-H), 6.04 (1H, d, 7-H) 6.24 (1H, d, 6-H).

To a stirred solution of vitamin $D_4$ (IX) (3.0 g, 7.5 mmol) in 10 ml of dry pyridine was added freshly recrystallized p-toluenesulfonyl chloride (3.6 g, 19 mmol) at 0° C. The reaction mixture was stirred at 5° C. for 24 hours, and was then quenched by pouring the mixture over ice and saturated $NaHCO_3$ (100 ml) with stirring. The aqueous suspension was extracted with $CH_2Cl_2$ (3×300 ml). The combined organic extracts were washed with 10% HCl (3×200 ml), saturated $NaHCO_3$ (3×200 ml) and saturated NaCl (2×200 ml), dried over $MgSO_4$ and concentrated in vacuo to yield 3.5 g. (84%) of the novel intermediate compound vitamin $D_4$ tosylate (X) and had the following characteristics: $^1$H NMR (400 MHz, $CDCl_3$), δppm 0.54 (3H, s, 18-$H_3$) 0.78 (6H, dd, 26-$H_3$ and 27-$H_3$) 0.87 (3H, d, 21-$H_3$), 0.96 (3H, d, 28-$H_3$) 2.45 (3H, s, $CH_3$ (tosylate) 4.68 (3H, m, 3-H) 4.82 (1H, m (sharp), 19-H) 5.04 (1H, m (sharp), 19-H), 5.95 (1H, d 7-H), 6.09 (1H, d, 6-H) 7.34 and 7.79 (4H, d, aromatic).

To a stirred suspension of $NaHCO_3$ (17.0 g, 202 mmol) in methanol (200 ml) a solution of vitamin $D_4$ tosylate (X) (3.5 g, 6.3 mmol) in dry $CH_2Cl_2$ (10 ml) was added dropwise. The reaction mixture was refluxed overnight under argon, and then cooled to room temperature and concentrated in vacuo to about 50 ml. The reaction concentrate was diluted with ether (600 ml), washed with water (3×300 ml), dried over $MgSO_4$ and concentrated in vacuo. The residue was passed through a silica gel column and eluted with 10% ethyl acetate in hexane to afford the novel intermediate compound 3,5 cyclovitamin $D_4$ (XI) (heavy oil) with a yield of 1.5 g. (58%) and had the following characteristics: $^1$H NMR (400 MHz, $CDCl_3$), δppm 0.56 (3H, s, 18-$H_3$) 0.78 (6H, dd, 26-$H_3$ and 27-$H_3$), 0.87 (3H, d, 21-$H_3$), 0.94 (3H, d, 28-$H_3$), 3.28 (3H, s, $OCH_3$) 4.2 (1H, d, 6-H), 4.91 (1H, m (sharp), 19-1), 4.98 (1H, d 7-H), 5.08 (1H, m (sharp), 19-H).

Anhydrous tert-butyl hydroperoxide in toluene (3M) (2.6 ml, 7.8 mmol) was added to a stirred suspension of selenium dioxide (0.22 g, 2 mmol) in dry $CH_2Cl_2$ (150 ml) in a three necked flask. The mixture was stirred for three hours under argon. Pyridine (0.3 ml, 3.7 mmol) was then added, and cyclovitamin $D_4$ (XI) (1.5 g, 3.6 mmol) was then introduced as a solution in $CH_2Cl_2$ (50 ml). After stirring for thirty minutes, 10% aqueous NaOH solution (200 ml) was added. The reaction mixture was then diluted with ether (500 ml) and the phases were separated. The organic phase was washed with 10% NaOH (3×200 ml), water (2×200 ml) and saturated NaCl solution (2×200 ml), dried over $MgSO_4$ and concentrated in vacuo. The residue was absorbed on a silica gel column and eluted with 30% ethyl acetate in hexane to afford 0.45 g. (29%) of the novel intermediate compound 1α-hydroxy 3,5-cyclovitamin $D_4$ (XII) (oil) and had the following characteristics: $^1$H NMR (400 MHz, $CDCl_3$) δppm 0.54 (3H, s, 18-$H_3$) 0.78 (6H, dd, 26-$H_3$ and 27-$H_3$) 0.86 (3H, d, 21-$H_3$) 0.95 (3H, d, 28-$H_3$) 3.26 (3H, s, $OCH_3$) 4.2 (1H, d, 6-H), 4.22 (1H, m, 1-H), 4.95 (1H, d 7-H), 5.18 (1H, d, 19-H) 5.25 (1H, d, 19-H).

A solution of 1α-hydroxy 3,5-cyclovitamin $D_4$ (XII) (0.45 g, 1.05 mmol) in a solution of dimethyl sulfoxide (4.5 ml) and glacial acetic acid (3.6 ml) was heated to 50° C. under argon for one hour. The reaction mixture was then poured over ice and saturated $NaHCO_3$ solution (100 ml), and extracted with ether (3×200 ml). The combined ether extracts were washed with saturated $NaHCO_3$ solution (3×200ml), water (3×200 ml) and saturated NaCl solution (3×200 ml), dried over $MgSO_4$, concentrated in vacuo to give a mixture containing 5,6-cis and 5,6-trans 1α-hydroxy vitamin $D_4$ (about 4:1 by $^1$H NMR) with a yield of 0.4 g, (92%). The mixture of 5,6-cis and 5,6-trans 1α-hydroxy vitamin $D_4$ (0.4 g, 0.97 mmol) was dissolved in ethyl acetate (25 ml) and treated with freshly recrystallized maleic anhydride (0.08 g, 0.8 mmol). This reaction mixture was heated to 35° C. under argon for 24 hours. After evaporation of the solvent in vacuo, the crude mixture was chromatographed over a silica gel column using ethyl acetate and hexane (1:1) as eluent, to afford the novel active form of vitamin $D_4$, 5,6-cis 1α-hydroxy vitamin $D_4$ (XIII) with a yield of 90 mg (23%) and had the following characteristics: m.p.:

128°–130° C.; IR $v_{max}$ (Neat): 3400 cm$^{-1}$ (OH stretching); $^1$H NMR (400 MHz, CDCl$_3$), δppm 0.55 (3H, s, 18-H) 0.79 (6H, dd, 26-H$_3$ and 27-H$_3$) 0.87 (3H, d, 21-H$_3$) 0.94 (3H, d, 28-H$_3$), 4.24 (1H, m, 3-H), 4.44 (1H, m, 1-H), 5.02 (1H, m (sharp), 19-H), 5.34 (1H, m (sharp), 19-H), 6.02 (1H, d 7-H), 6.4 (1H, d, 6-H); Mass spectrum [CI] m/e (relative intensity): 415 (M+1, 41%) 397, (M+1-OH 100%), 379 (27%), 135 (22%).

EXAMPLE 2

Biological Testing of 1α-hydroxy vitamin D$_4$

Male weanling rats (Holtzman strain, Holtzman Company, Madison, Wis.) were fed a vitamin D deficient diet containing adequate calcium (0.47%) and phosphorus (0.3%). Within three to four weeks, this diet induces an extreme vitamin D deficiency characterized by low serum calcium an d poor growth. After four weeks on this diet, the rats had serum calcium values less than 7 mg/dl. The rats were then separated into four groups and orally administeredeither 1α-hydroxy vitamin D$_4$ in a vehicle such as coconut oil or the vehicle (control) for each of 14 days. Twenty-four hours after the last dose, the rats were killed and the blood calcium measured by a standard laboratory technique. The results of these determinations are shown in Table 1.

TABLE 1

Increase in Serum Calcium Concentration

| Compound | Dose (µg/kg/day) | Number of rats | Serum calcium concentration (mg/dl) ± Standard Deviation |
|---|---|---|---|
| Control | — | 10 | 6.1 ± 0.48 |
| 1α-OH-D$_4$ | 0.042 | 8 | 7.1 ± 0.80 |
| 1α-OH-D$_4$ | 0.250 | 7 | 11.6 ± 0.45 |
| 1α-OH-D$_4$ | 1.500 | 9 | 12.7 ± 0.37 |

The data of Table 1 indicate that 1α-hydroxy vitamin D$_4$ is effective at increasing serum calcium in the vitamin D deficient rat and that the response appears to be dose dependent. Surprisingly, the level of th e response appears to compare favorably to that reported by Wientroub, et. al., for 1,25 dihydroxy vitamin D$_3$ administered to vitamin D deficient rats under experimental conditions similar to those described above. See, Wientroub, S., Price, P. A., Reddi, A. H., "The Dichotomy in the Effects of 1,25 dihydroxy vitamin D$_3$ and 24,25 dihydroxy vitamin D$_3$ on Bone Gamma-Carboxyglutamic Acid-Containing Protein in Serum and Bone in vitamin D-Deficient Rats," *Calcif. Tissue Int.* (1987) 40:166–172.

EXAMPLE 3

Toxicity Tests

The acute oral toxicity of 1α—OH—D, in rats was assessed by determining the mean lethal dose (LD$_{50}$) using a well-known method. Rats were fed a standard laboratory diet for 8–10 weeks. Five animals of each sex were administered one oral dose of 1α—OH—D$_4$. The animals were observed for 14 days, and the number of deaths noted. The LD$_{50}$ value was determined to be about 1.0 mg/kg in males and 3.0 mg/kg in females.

For comparison, the LD$_{50}$ value for 1α-hydroxy vitamin D$_2$ under the same conditions was found by applicant's to be 1.7 and 1.8 mg/kg. in male and female rats, respectively. The toxicity of 1α-hydroxy vitamin D$_2$ has previously been reported as less than 1α-hydroxy vitamin D$_3$. Sjoden, G., Smith, C., Lindgren, U., and DeLuca, H. F., *Proc. Soc. Experimental Biol. Med.*, 178:432–436 (1985).

EXAMPLE 4

Generation and Isolation of 1,25-dihydroxy vitamin D$_4$

The 1α-hydroxy vitamin D$_4$ of the present invention is incubated with cultured human liver cells which metabolize the compound to several products including the metabolite 1,25 dihydroxy vitamin D$_4$. The 1,25 metabolite is isolated and purified by high pressure liquid chromatography and identified by gas-chromatography-mass spectrometry. Binding studies demonstrate that the 1,25 dihydroxy vitamin D$_4$ has good binding affinity for the mammalian vitamin D receptor protein indicating it is biologically active. The procedures used are similar to that described by Strugnell, et. al., *Biochem. Pharm.* Vol. 40:333–341 (1990).

EXAMPLE 5

Generation and Isolation of 1,24-dihydroxy vitamin D$_4$

Generation and isolation of 1,24 dihydroxy vitamin D$_4$ is accomplished as described in Example 4, above. The 1α-hydroxy vitamin D$_4$ of the present invention is incubated with cultured human liver cells which metabolize the compound to several products including the metabolite 1,24 dihydroxy vitamin D$_4$. The 1,24 metabolite is isolated and purified using high pressure liquid chromatography and identified by gas-chromatography-mass spectrometry. Binding studies with the new metabolite demonstrate that the metabolite has good binding affinity for the mammalian vitamin D receptor protein which indicates the drug is biologically active.

EXAMPLE 6

Hypercalcemia Testing

Female rats are fed a commercial diet containing 0.8% calcium (0.8%) and phosphorus (0.6%). The rats are divided into four groups and each group is orally administered daily either (1α-OH D$_4$ in a vehicle such as coconut oil or the vehicle (control) alone for 13 weeks. Twenty-four hours after the last dose, the rats are killed and their serum calcium determined by a standard method.

This procedure demonstrates that the serum calcium concentration is unaffected or only slightly elevated at doses 1α—OH—D$_4$ up to 2.5 µg/kg/day.

EXAMPLE 7

Further Biological Testing

Male weanling rats are fed a diet deficient in vitamin D and with low calcium (0.02%). After a period of four weeks has elapsed, the rats are divided into four groups and intravenously administered either 1α-OH D$_4$ in a vehicle such as ethanol or the vehicle (control) alone. Sixteen hours after administration, the rats are killed and the intestinal calcium transport measured by using everted duodenal sacs, following the method of Martin and DeLuca, *Am. J. Physiol.* 216:1352–1359.

Following this procedure demonstrates stimulation of intestinal calcium transport in a dose dependent manner.

EXAMPLE 8

A clinical study is conducted with postmenopausal osteoporotic outpatients having ages between 55 and 75 years. The study involves up to 120 patients randomly divided into three treatment groups, and continues for 12 to 24 months. Two of the treatment groups receive constant dosages of 1α-vitamin $D_4$ (u.i.d.; two different dose levels above 3.0 μg/day) and the other group receives a matching placebo. All patients maintain a normal intake of dietary calcium (500 to 800 mg/day) and refrain from using calcium supplements. Efficacy is evaluated by pre- and post-treatment comparisons of the patient groups with regard to (a) total body, radial, femoral and/or spinal bone mineral density as determined by x-ray absorptiometry (DEXA), (b) bone biopsies of the iliac crest, and (c) determinations of serum osteocalcin. Safety is evaluated by comparisons of urinary hydroxyproline excretion, serum and urine calcium levels, creatinine clearance, blood urea nitrogen, and other routine determinations.

This study demonstrates that patients treated with 1α-vitamin $D_4$ exhibit significantly higher total body, radial, femoral and/or spinal bone densities relative to patients treated with placebo. The treated patients also exhibit significant elevations in serum osteocalcin. Bone biopsies from the treated patients show that 1α-vitamin $D_4$ stimulates normal bone formation. The monitored safety parameters confirm an insignificant incidence of hypercalcemia or hypercalciuria, or any other metabolic disturbance with 1α-vitamin $D_4$ therapy.

EXAMPLE 9

A clinical study is conducted with healthy postmenopausal women having ages between 55 and 60 years. The study involves up to 80 patients randomly divided into two treatment groups, and continues for 12 to 24 months. One treatment group receives a constant dosage of 1α-vitamin $D_4$ (u.i.d.; a dose level above 3.0 μg/day) and the other receives a matching placebo. The study is conducted as indicated in Example 8 above.

This study demonstrates that patients treated with 1α-vitamin $D_4$ exhibit reduced losses in total body, radial, femoral and/or spinal bone densities relative to baseline values. In contrast, patients treated with placebo show significant losses in these parameters relative to baseline values. The monitored safety parameters confirm the safety of long-term 1α-vitamin $D_4$ administration at this dose level.

EXAMPLE 10

A twelve-month double-blind placebo-controlled clinical trial is conducted with thirty men and/or women with renal disease who are undergoing chronic hemodialysis. All patients enter an eight-week control period during which time they receive a maintenance dose of vitamin $D_3$ (400 IU/day). After this control period, the patients are randomized into two treatment groups: one group receives a constant dosage of 1α-vitamin $D_4$ (u.i.d.; a dosage greater than 3.0 μg/day) and the other group receives a matching placebo. Both treatment groups receive a maintenance dosage of vitamin $D_3$, maintain a normal intake of dietary calcium, and regrain from using calcium supplements. Efficacy is evaluated by pre- and post-treatment comparisons of the two patient groups with regard to (a) direct measurements of intestinal calcium absorption, (b) total body, radial, femoral and/or spinal bone mineral density, and (c) determinations of serum calcium and osteocalcin. Safety is evaluated by regular monitoring of serum calcium.

Analysis of the clinical data shows that 1α-vitamin $D_4$ significantly increases serum osteocalcin levels and intestinal calcium absorption, as determined by measurements using a single or double-isotope technique. Patients treated with this compound show normalized serum calcium levels, stable values for total body, radial, femoral and/or spinal bone densities relative to baseline values. In contract, patients treated with placebo show frequent hypocalcemia, significant reductions in total body, radial, femoral and/or spinal bone density. An insignificant incidence of hypercalcemia is observed in the treated group.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can-be accorded the appended claims.

We claim:

1. A method of treating osteoporosis, comprising administering to a patient suffering therefrom an amount effective to treat the osteoporosis of a compound of the formula (I)

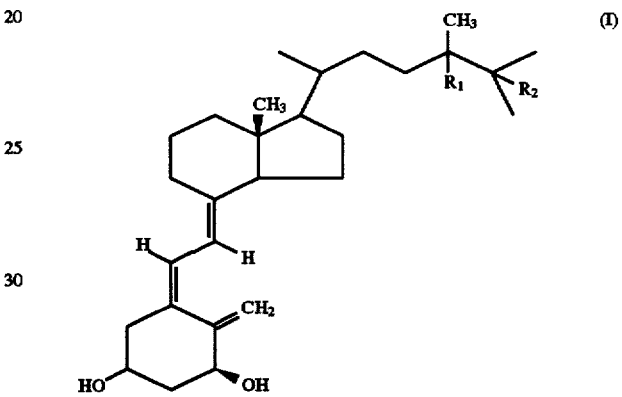

wherein $R_1$ is either H or OH and $R_2$ is either H or OH.

2. A method of treating osteoporosis, comprising administering to a patient suffering therefrom an effective amount of 1α,24-dihydroxyvitamin $D_4$.

3. The method of claim 1 wherein said compound of formula (I) is 1α-hydroxyvitamin $D_4$.

4. The method of claim 1, wherein said amount of the compound of formula (I) is administered in a daily dosage of about 0.04 μg/kg to about 0.3 μg/kg.

5. The method of claim 1, further comprising a therapeutic agent selected from the group consisting of estrogen, bisphosphonate and combinations thereof.

6. The method of claim 1, further comprising continuing said administering step until bone mass increases and the patient's calcium balance becomes positive, thereby indicating mineral accumulation in the patient's skeleton.

7. The method of claim 2, wherein said amount is at least 3 μg/day.

8. The method of claim 2, wherein said administering of said amount of 1α,24-dihydroxyvitamin $D_4$ is substantially without the occurrence of hypercalcemia, said amount being at least 2.5 μg/day.

9. The method of claim 2, further comprising administering a therapeutic agent selected from the group consisting of estrogen, bisphosphonate and combinations thereof.

10. The method of claim 2, further comprising continuing said administering step until bone mass increase and the patient's calcium balance become positive, thereby indicating mineral accumulation in the patient's skeleton.

11. The method of claim 2 wherein said administering step comprises orally administering 1α,24-dihydroxyvitamin $D_4$.

* * * * *

UNITED STATES PATENT AND TRADEMARK OFFICE
CERTIFICATE OF CORRECTION

PATENT NO. : 5,801,164
DATED : September 1, 1998
INVENTOR(S) : Knutson et al.

Page 1 of 1

It is certified that error appears in the above-identified patent and that said Letters Patent is hereby corrected as shown below:

Column 2,
Line 28, "The-present" should read -- The present --.

Column 3,
Line 27, "$R_1H$" should read -- $R_1 = H$ --.
Line 36, "windaus" should read -- Windaus --.

Column 4,
Line 31, after the term wherein", insert -- $R^1$ or --.
Line 64, "D2" should read -- $D_2$ --.

Column 9,
Line 18, "an d" should read -- and --.
Line 21, "teredeither" should read -- tered either --.
Line 42, "th e" should read -- the --.

Column 11,
Line 56, "regrain" should read -- refrain --.

Column 12,
Line 2, "contract" should read -- contrast --.
Lines 17-18, "an amount effective to treat the osteoporosis" should read -- an effective amount --.

Signed and Sealed this

Eighteenth Day of December, 2001

*Attest:*

*Attesting Officer*

JAMES E. ROGAN
*Director of the United States Patent and Trademark Office*